United States Patent
Sato et al.

(10) Patent No.: US 9,555,421 B2
(45) Date of Patent: Jan. 31, 2017

(54) SORTING APPARATUS AND SORTING METHOD

(71) Applicant: Sony Corporation, Tokyo (JP)

(72) Inventors: Kazumasa Sato, Tokyo (JP); Yoichi Katsumoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 65 days.

(21) Appl. No.: 14/161,880

(22) Filed: Jan. 23, 2014

(65) Prior Publication Data

US 2014/0262970 A1   Sep. 18, 2014

(30) Foreign Application Priority Data

Mar. 13, 2013 (JP) ................................. 2013-050316

(51) Int. Cl.
  *B03C 7/02* (2006.01)
  *B03C 5/00* (2006.01)
  *B03C 5/02* (2006.01)

(52) U.S. Cl.
  CPC .............. *B03C 5/005* (2013.01); *B03C 5/026* (2013.01); *B03C 2201/26* (2013.01)

(58) Field of Classification Search
  CPC ............ B03C 5/005; B03C 5/026; B03C 5/00; B01L 2400/0424; G01N 27/221; G01N 27/447; B01D 57/02
  See application file for complete search history.

(56) References Cited

U.S. PATENT DOCUMENTS

| | | | | |
|---|---|---|---|---|
| 2004/0112748 A1* | 6/2004 | Lee | .......................... | B03C 5/026 204/547 |
| 2010/0006439 A1* | 1/2010 | Ham et al. | ......... | B01L 3/502761 204/547 |
| 2012/0273357 A1* | 11/2012 | Katsumoto | ......... | G01N 15/1404 204/547 |

FOREIGN PATENT DOCUMENTS

JP    2012-098075    5/2012

OTHER PUBLICATIONS

Geheb et al., IEEE Transactions on Biomedical Circuits and Systems, vol. 3, 2009, 1-11.*
Granta-definition of permittivity.*

* cited by examiner

*Primary Examiner* — Gurpreet Kaur
(74) *Attorney, Agent, or Firm* — Chip Law Group

(57) ABSTRACT

Provided is a sorting apparatus including: a flow channel device including a flow channel through which a fluid including particles flows and an operation electrode portion that causes a dielectrophoretic force to act on the particles in the flow channel; and a controller configured to detect characteristics of the particles flowing through the flow channel, generate a voltage signal by a pulse modulation using a square pulse based on the detected characteristics of the particles, and output the voltage signal to the operation electrode portion.

10 Claims, 14 Drawing Sheets

|  | 1MHz | 2.5MHz | 5MHz |
|---|---|---|---|
| Peak speed [μm/s] | 40.8 | 93.0 | 167.8 |
| Δy/Δx | 0.00568 | 0.0129 | 0.0234 |

FIG.14

SORTING APPARATUS AND SORTING METHOD

CROSS REFERENCE TO RELATED APPLICATIONS

This application claims the benefit of Japanese Priority Patent Application JP 2013-050316 filed Mar. 13, 2013, the entire contents of which are incorporated herein by reference.

BACKGROUND

The present disclosure relates to a sorting apparatus and a sorting method for sorting particles of cells and the like using a dielectrophoretic force.

From the past, as a method of sorting particles in a fluid by an electromagnetic force, there are the following two methods, for example. One is a method of performing an electrophoresis of charge particles by forming a DC electric field in a flow channel. The other is a method of performing an electrophoresis of particles while depending on a complex permittivity of a medium and particles by forming a DC or AC electric field in a flow channel and giving a spatial heterogeneity, that is, an electric field intensity gradient to the electric field. As an example of the latter method of performing an electrophoresis, there is a cell sorting apparatus (cell analysis/sorting system) disclosed in Japanese Patent Application Laid-open No. 2012-98075 (hereinafter, referred to as Patent Document 1).

The cell sorting apparatus includes a cell sorting chip that includes a micro flow channel, for example. This apparatus measures, when a fluid including cells flows through predetermined flow channels in the chip, a complex impedance and a complex permittivity among the flow channels and sorts the cells based on the measurement result. The chip includes a signal detection electrode (measurement portion) for measuring a complex impedance and a complex permittivity of cells and detecting signals. The chip also includes as a cell sorting means, on a downstream side of the signal detection electrode, an operation electrode (electric field application portion) having a predetermined shape, that is provided for forming a DC or AC electric field for imparting an appropriate dielectrophoretic force to the cells (see, for example, paragraphs (0025), (0028), etc. in specification of Patent Document 1).

SUMMARY

While a voltage amplitude needs to be controlled for controlling a movement amount of particles by the dielectrophoretic force, since the voltage is a high voltage of a high frequency, it is difficult to control the voltage amplitude, and thus an expensive circuit is required.

Therefore, there is a need for a sorting apparatus and a sorting method with which an output voltage with respect to an operation electrode can be controlled with ease using an inexpensive circuit.

According to an embodiment of the present disclosure, there is provided a sorting apparatus including a flow channel device and a controller.

The flow channel device includes a flow channel through which a fluid including particles flows and an operation electrode portion that causes a dielectrophoretic force to act on the particles in the flow channel.

The controller is configured to detect characteristics of the particles flowing through the flow channel, generate a voltage signal by a pulse modulation using a square pulse based on the detected characteristics of the particles, and output the voltage signal to the operation electrode portion.

Since the controller generates the voltage signal by the pulse modulation using the square pulse for causing a dielectrophoretic force by an electric field intensity gradient in the flow channel, a pulse modulation circuit can be structured by an inexpensive circuit, and an output voltage with respect to the operation electrode can be controlled with ease.

The flow channel device may include a measurement electrode portion that measures electrical characteristics of the particles, and the controller may detect the characteristics of the particles based on a signal obtained by the measurement electrode portion. In this case, the controller may calculate a complex permittivity based on the signal obtained by the measurement electrode portion and generate the voltage signal based on the complex permittivity. By using the complex permittivity, sorting accuracy can be improved.

The controller may generate the voltage signal by PDM (Pulse Density Modulation), or generate the voltage signal by PWM (Pulse Width Modulation).

The controller may use a square pulse having a predetermined frequency range of 0.1 MHz or more and 100 MHz or less. The predetermined frequency range may be fixed or may be variable.

By causing the dielectrophoretic force using the voltage signal generated by the pulse modulation using the square pulse, a minute displacement can be imparted to the particles in a small flow channel.

The operation electrode portion may include a plurality of electrode fingers to which the voltage signal is applied, the plurality of electrode fingers being aligned along a direction in which the fluid flows, and an opposing electrode opposing the plurality of electrode fingers. By arranging the plurality of electrode fingers in the direction in which the fluid flows, an electric field intensity gradient can be generated between the plurality of electrode fingers and the opposing electrode.

The opposing electrode may surround at least a part of a circumference of the plurality of electrode fingers such that a distance between tip ends of the plurality of electrode fingers and the opposing electrode becomes constant. With this structure, when the plurality of electrode fingers are provided successively in the direction in which the fluid flows, electric flux densities in the same state are aligned for each of the plurality of electrode fingers. Therefore, the operation electrode portion can impart minute displacements stepwise in a direction in which the dielectrophoretic force acts little at a time.

According to an embodiment of the present disclosure, there is provided a sorting method for sorting particles using a flow channel device including a flow channel through which a fluid including the particles flows and an operation electrode portion that causes a dielectrophoretic force to act on the particles in the flow channel.

Characteristics of the particles flowing through the flow channel are detected.

A voltage signal is generated by a pulse modulation using a square pulse based on the detected characteristics of the particles, and the voltage signal is output to the operation electrode portion.

As described above, according to the embodiments of the present disclosure, the output voltage can be controlled with ease using an inexpensive circuit.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 14 is a table showing mean values of the particle displacement amounts ($\Delta y/\Delta x$) and the particle speeds in the y direction for each of the set frequencies regarding the experiment shown in FIGS. 12 and 13;

DETAILED DESCRIPTION OF EMBODIMENTS

Hereinafter, embodiments of the present disclosure will be described with reference to the drawings.

First Embodiment

Structure of Sorting Apparatus

Figure 1:
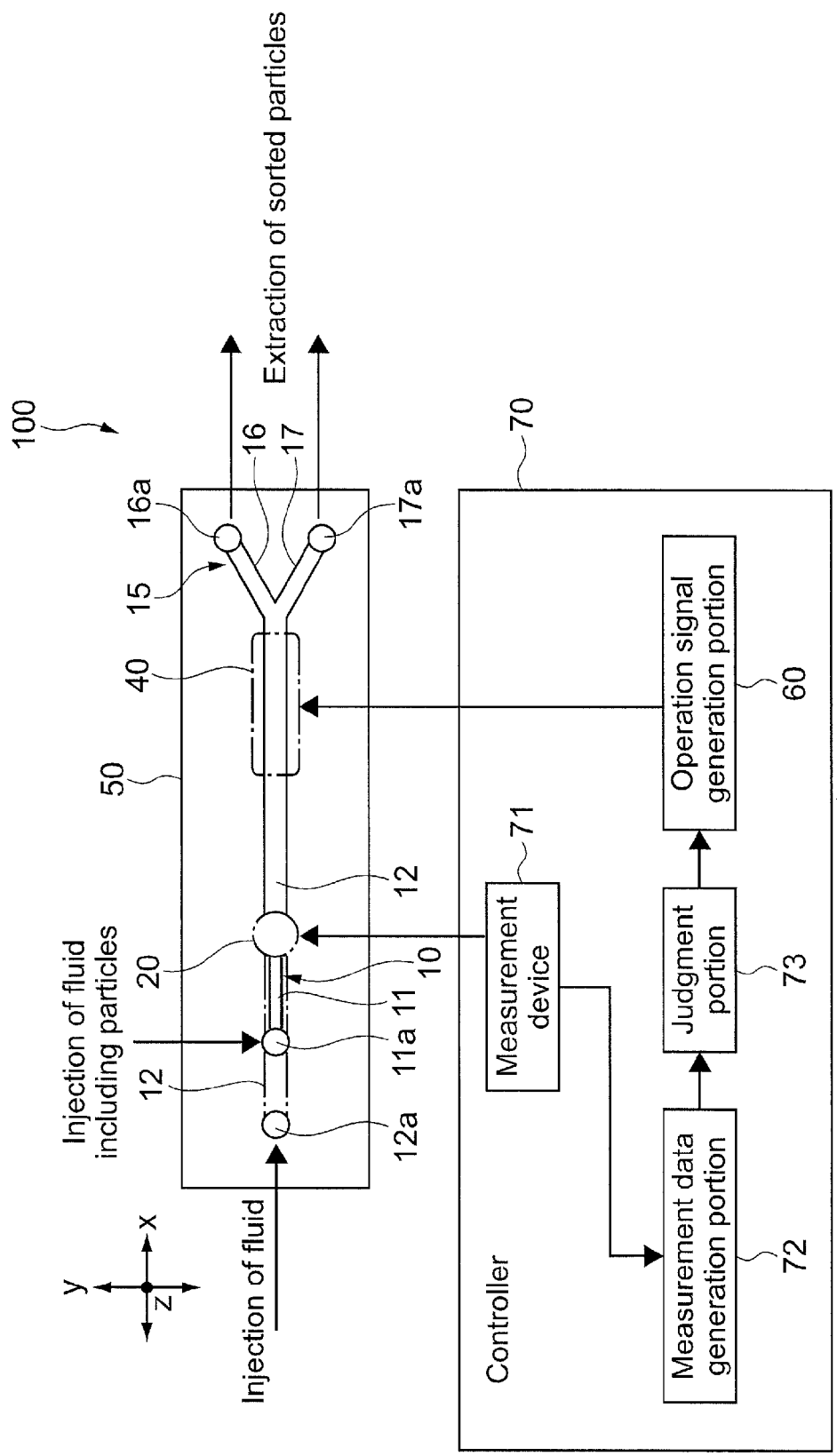
FIG. 1 is a block diagram showing a structure of a sorting apparatus according to a first embodiment of the present disclosure.

FIG. 1 is a block diagram showing a structure of a sorting apparatus according to a first embodiment of the present disclosure. The sorting apparatus 100 includes a flow channel device 50 and a controller 70.

The flow channel device 50 is formed in, for example, a chip shape and includes a flow channel 10. Through the flow channel 10, a fluid including particles as a sample flows. The flow channel 10 is a micro flow channel having a small width of about 30 to 200 μm, for example. The flow channel device 50 includes, from an upstream side on the left-hand side of the figure, a measurement electrode portion 20, an operation electrode portion 40, and a branch portion 15 along the flow channel 10.

The particles as a sample are, for example, biological cells, that is, leucocytes and erythrocytes. When the particles are cells, a normal saline solution or the like is selected as the fluid.

Figure 2:
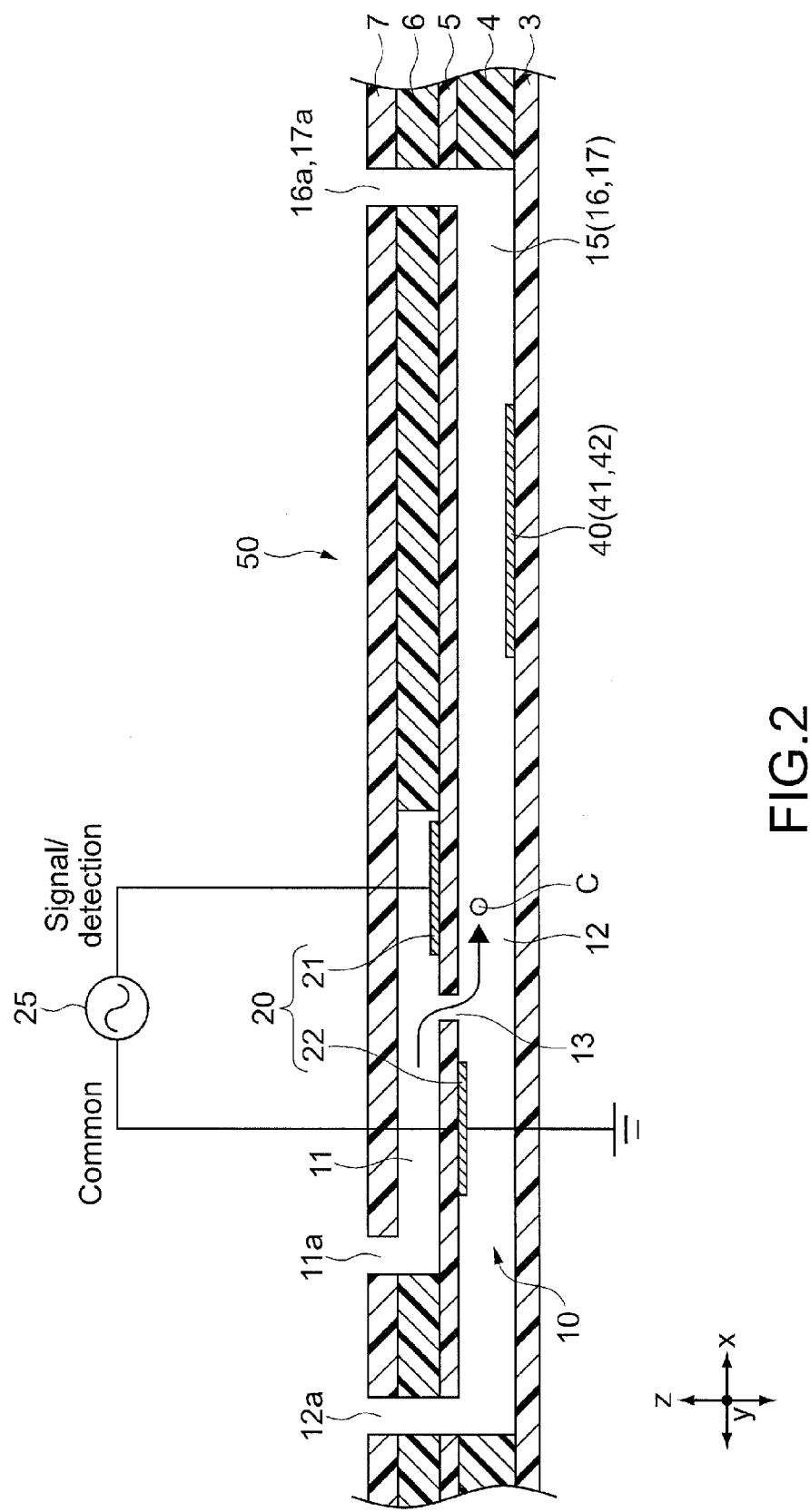
FIG. 2 is a schematic cross-sectional diagram of a flow channel device taken along a direction of a flow channel.

FIG. 2 is a schematic cross-sectional diagram of the flow channel device 50 taken along a direction of the flow channel 10. The flow channel device 50 includes the 2-stage flow channel 10 in a thickness direction of the flow channel device 50. In FIG. 2, a first flow channel 11 provided on an upstream side includes a first inlet 11a, and a fluid including particles C is caused to flow into the first flow channel 11 via the first inlet 11a using a pipette, a pump, and the like (not shown). Since the particles are aligned along a flowing direction in the first flow channel 11, it is favorable to cause the fluid to flow into the first inlet 11a at a constant flow rate using a syringe pump or the like.

A second flow channel 12 provided on a downstream side includes a second inlet 12a, and a fluid not including particles is caused to flow into the second flow channel 12 via the second inlet 12a using a pump or other apparatuses (not shown). It is favorable for the pressure of the fluid that flows into the second flow channel 12 via the second inlet 12a to be constant.

Figure 3:
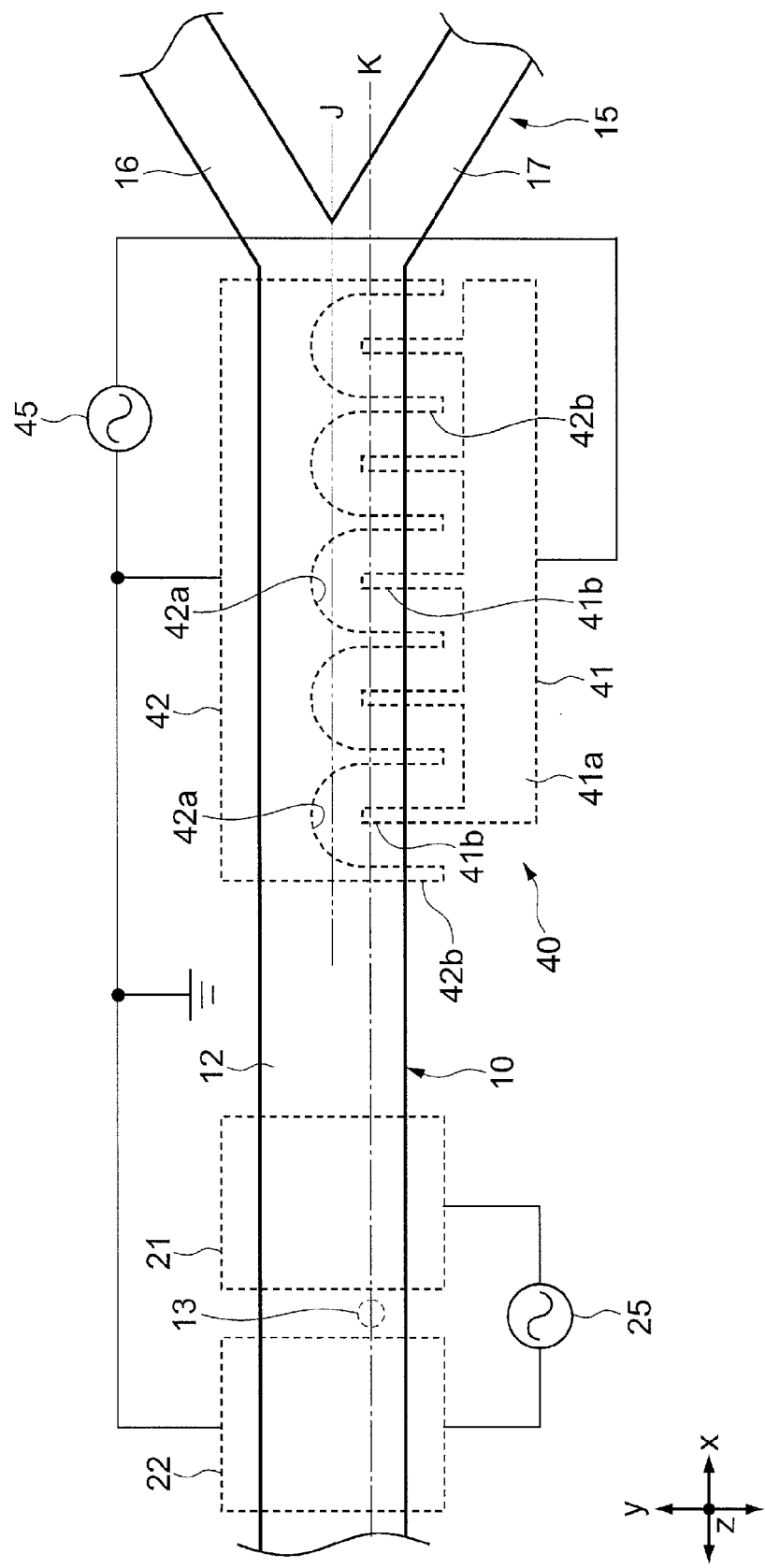
FIG. 3 is a plan view of a second flow channel and a branch portion branching from the second flow channel.

FIG. 3 is a plan view of the second flow channel 12 and the branch portion 15 branching from the second flow channel 12. The second flow channel 12 is formed to be longer than the first flow channel 11 and is formed practically in a Y shape. The portion formed in the Y shape is the branch portion 15, which includes a plurality of (e.g., two) branch channels 16 and 17. At downstream end portions of the branch channels 16 and 17, outlets 16a and 17a are provided as shown in FIG. 1. It should be noted that a pool (not shown) for pooling sorted particles may be provided in place of the outlets 16a and 17a, and one or more outlets for taking out the particles pooled in the pool may be provided on the downstream side of the pool.

As shown in FIGS. 2 and 3, the first flow channel 11 and the second flow channel 12 are in communication with each other via a narrowed channel 13. As shown in FIG. 3, the narrowed channel 13 is provided on, for example, a line K at a position deviated from a center of the second flow channel 12 (position of branch reference line J) in a y direction as a width direction.

As described above, by splitting the flow channel 10 into the first flow channel 11 and the second flow channel 12, an alignment of the particles C can be promoted by a constant flow rate in the first flow channel 11 and the narrowed channel 13, and a pressure gradient of the fluid in the second flow channel 12 can be determined dominantly in the second flow channel 12. Accordingly, since a stability of a fluid pressure at an outlet portion of the narrowed channel 13 can be enhanced, a flow rate of the fluid that passes the narrowed channel 13 can be stabilized. As a result, measurement accuracy of electrical characteristics of the particles by the measurement electrode portion 20 can be improved.

It should be noted that the terms "up" and "down" are irrelevant to the gravity direction. In the specification, the terms "up" and "down" are used for convenience.

In FIG. 1, the first flow channel 11 on the upstream side and the second flow channel 12 on the downstream side are parallel in the x direction and overlap each other in a plan view. However, the structure is not limited to such a structure, and the direction of the flow channels 10 does not need to be parallel and/or the flow channels do not need to overlap each other in a plan view. In other words, as long as the first flow channel 11 and the second flow channel 12 are connected via the narrowed channel 13, the flow channels 10 may be formed in any direction. In this case, a drainage channel or a drainage outlet may be connected to only the first flow channel 11.

As shown in FIGS. 2 and 3, the narrowed channel 13 described above is provided at a predetermined position between the first flow channel 11 and the second flow channel 12. The narrowed channel 13 has a flow channel size enough for a single particle to flow through, for example, and the particles that flow through the first flow channel 11 flow into the second flow channel 12 via the narrowed channel 13.

As shown in FIGS. 2 and 3, the measurement electrode portion 20 includes measurement electrodes 21 and 22 sandwiching the narrowed channel 13. The measurement electrodes 21 and 22 are electrodes for measuring electrical characteristics when the particles pass through the narrowed channel 13. The measurement electrodes 21 and 22 are provided on upper and lower surfaces of a center resin film 5 out of resin films 3 to 7 laminated as shown in FIG. 2, for example, and constitute a parallel plate capacitor. An AC power supply 25 is connected to the measurement electrodes 21 and 22 so that a predetermined AC voltage of a several-hundred mV order can be applied. The measurement electrode 22 is a common electrode.

Figure 4:
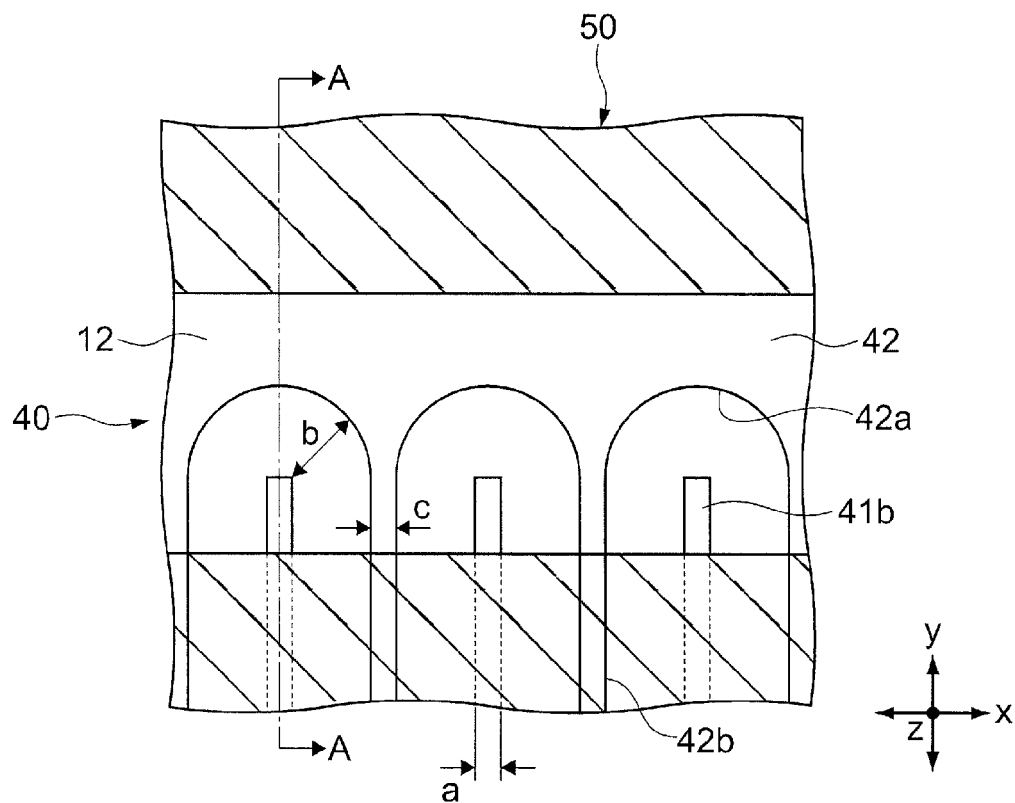
FIG. 4 is a plan view showing a part of an operation electrode portion.
Figure 5:
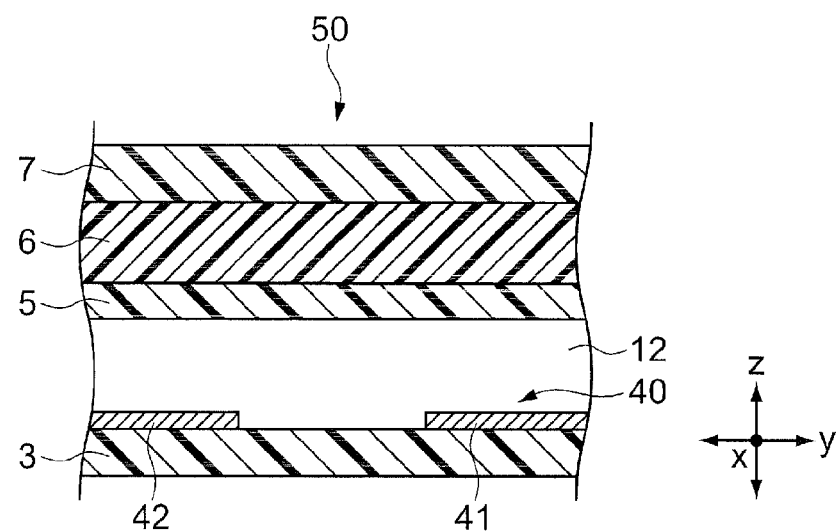
FIG. 5 is a cross-sectional diagram taken along the line A-A of FIG. 4.

The operation electrode portion 40 is provided on the upstream side of the branch portion 15, specifically, right before the branch portion 15, and forms an electric field having a predetermined electric field intensity gradient so as to impart a dielectrophoretic force to the particles flowing through the flow channel 10. FIG. 4 is a plan view showing a part of the operation electrode portion 40, and FIG. 5 is a cross-sectional diagram taken along the line A-A of FIG. 4.

The operation electrode portion 40 includes operation electrodes 41 and 42. As shown in FIG. 5, the operation electrodes 41 and 42 are provided on a bottom surface of the second flow channel 12 (upper surface of resin film 3). An AC power supply 45 is connected to the operation electrodes 41 and 42 as shown in FIG. 3 so that an AC voltage (operation voltage) is applied between the operation electrodes 41 and 42. The operation electrode 41 is a signal electrode to which an operation signal is applied, and the operation electrode 42 is a common electrode maintained at a ground potential. It should be noted that the operation electrode 42 may be a signal electrode, and the operation electrode 41 may be a common electrode.

As shown in FIG. 3, the operation electrode 41 is formed in a comb shape and includes a base portion 41a and a plurality of electrode fingers 41b elongated so as to protrude into the second flow channel 12 from the base portion 41a. The electrode fingers 41b are aligned along the x direction, and portions including tip end portions thereof protrude to the second flow channel 12 side.

The operation electrode 42 is also formed in a comb shape, and electrode fingers 42b thereof are aligned alternately with the electrode fingers 41b of the operation electrode 41 in the x direction. The operation electrode 42 is an opposing electrode opposing the electrode fingers 41b of the operation electrode 41. Between the electrode fingers 42b, edge portions 42a formed in a shape that surrounds at least a circumference of the tip end portions of the electrode fingers 41b in the x-y plane are provided respectively. The tip end portions of the electrode fingers 42b are provided outside the second flow channel 12, and the edge portions 42a are each formed by a practical semi-circle and straight lines continuous with the semi-circle in the second flow channel 12. The edge portions 42a are formed along a line such that distances between the edge portions 42a and the tip end portions of the electrode fingers 41b of the operation electrode 41 are an equidistance as much as possible, the edge portions 42a each including a portion shaped along a semi-circle, for example. The edge portions 42a are not limited to such a semi-circle, and shapes formed along an oval or a polygon may also be used.

As a production method for the flow channel device 50 as described above, there is a method as follows, for example.

For example, a plurality of resin films (insulator films), for example, 5 resin films 3, 4, 5, 6, and 7 (see FIG. 2) are prepared. The electrodes including the measurement electrodes 21 and 22 and the operation electrodes 41 and 42 are formed on, for example, two resin films 3 and 5 out of the 5 resin films 3 to 7. Further, for forming the flow channel 10, the branch channels 16 and 17, the narrowed channel 13, and the inlets and outlets on the resin films, for example, grooves and holes are formed at predetermined positions as necessary. The electrodes, grooves, holes, and the like may be formed by photolithography and photo-etching, or may be formed by laser processing. The 5 resin films 3 to 7 on which the electrodes, grooves, and holes have been formed are positioned, laminated, and subjected to heat pressure bonding, with the result that the flow channel device 50 as shown in FIG. 2 is formed.

The measurement electrodes 21 and 22 and the operation electrodes 41 and 42 may be formed of, for example, copper, silver, gold, platinum, nickel, zinc, titanium, or stainless steel, or may be formed by carrying out various types of plating processing on them.

As the materials for the resin films 3 to 7, a polyimide film, a thermoplastic polyimide film, PDMS (polydimethylsiloxane or dimethylpolysiloxane), acryl, PES (polyethersulfone), polycarbonate, polypropylene, polystyrene, polyimide, COP (cyclic olefin polymer), COC (cyclic olefin copolymer), and the like are used. In this embodiment, one of the materials above is selected as the common material for forming the resin films 3, 5, and 7, and a material different from that of the resin films 3, 5, and 7 is selected as the common material for forming the resin films 4 and 6.

Next, the controller 70 will be described. As shown in FIG. 1, the controller 70 is electrically connected to the measurement electrode portion 20 and the operation electrode portion 40, generates an operation signal based on a measurement signal obtained by the measurement electrode portion 20, and outputs an operation voltage corresponding to the signal to the operation electrode portion 40. Specifically, the controller 70 includes a measurement device 71, a measurement data generation portion 72, a judgment portion 73, and an operation signal generation portion 60. The controller 70 is typically constituted of a computer.

The elements such as the measurement device 71 and the measurement data generation portion 72 have a function of detecting characteristics of particles, which are electrical characteristics in this embodiment Specifically, the measurement device 71 applies an AC voltage of an arbitrary frequency within a predetermined frequency range to the measurement electrodes 21 and 22. When the particles pass the narrowed channel 13, a resistance value between the measurement electrodes 21 and 22 changes. The measurement device 71 detects a current flowing between the measurement electrodes 21 and 22. The measurement data generation portion 72 calculates a complex impedance from the current value. Specifically, the measurement data generation portion 72 calculates, with respect to individual cells flowing through the narrowed channel 13, across multipoint frequencies (3 points or more, typically about 10 to 20 points or more) within an AC voltage frequency range (e.g., 0.1 MHz to 50 MHz) at which a dielectric relaxation phenomenon occurs, a complex permittivity that depends on those cells as the electrical characteristics.

It should be noted that in actuality, the measurement data generation portion 72 calculates a complex permittivity by a known electric conversion expression based on the complex impedance calculated as described above, and obtains data including the complex permittivity as measurement data.

As an amount electrically equivalent to the complex permittivity, there are a complex impedance, a complex admittance, a complex capacitance, a complex conductance, and the like, those of which can be mutually converted by the simple known electric amount conversion described above. Moreover, the measurement of a complex impedance or a complex permittivity includes a measurement of only a real part or imaginary part.

The judgment portion 73 acquires the measurement data output from the measurement data generation portion 72 and judges whether the particles are to be sorted based on the measurement data, that is, whether the particles are to be guided to a predetermined one of the branch channels (branch channel 16 in this embodiment) of the branch portion 15. Specifically, the judgment portion 73 carries out the judgment processing by collating a judgment condition of data on a complex permittivity that has been arbitrarily set in advance in a memory for sorting desired particles with the measurement data.

The operation signal generation portion 60 generates an operation signal when the measurement target particles are to be sorted (here, particles to be guided to branch channel 16), and does not generate an operation signal otherwise. It is also possible for the operation signal generation portion 60 to not generate an operation signal when the measurement target particles are to be sorted and generate an operation signal otherwise.

Figure 6:
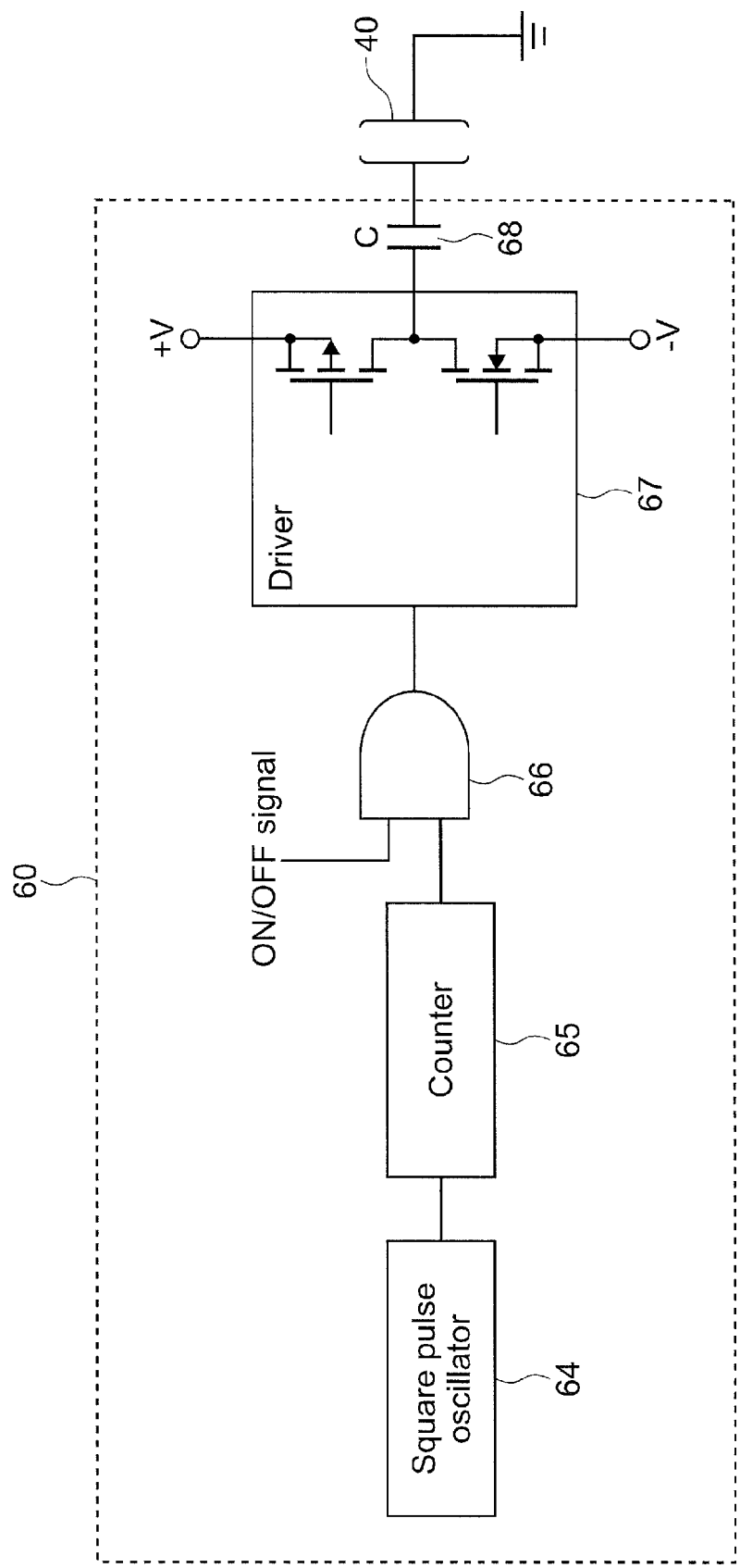
FIG. 6 is a block diagram showing a functional structure of an operation signal generation portion.

FIG. 6 is a block diagram showing a functional structure of the operation signal generation portion 60. The operation signal generation portion 60 is an apparatus that mainly generates an operation voltage signal by a pulse modulation that uses a square pulse, which is PDM (Pulse Density Modulation) in this embodiment. Specifically, the operation signal generation portion 60 includes a square pulse oscillator 64, a counter 65, a switch 66, a driver 67, and an AC coupling capacitor 68.

The square pulse oscillator 64 generates a square pulse of a favorable frequency for causing a dielectrophoretic force. The favorable frequency is 0.1 MHz or more and 100 MHz or less. The frequency may either be fixed or be variable. As the square pulse oscillator 64, for example, a PLL (Phase Locked Loop) oscillator that uses a crystal oscillator or a DDS (Direct Digital Synthesizer) oscillator is used.

The counter 65 counts a pulse count input from the square pulse oscillator 64 and outputs the pulse at a timing when the pulse count reaches a predetermined number of counts. In other words, a pulse-count drawing output is performed. As a result, the output pulse count per unit time is adjusted.

The switch 66 is a gate circuit that makes a switch between ON and OFF for the output.

The driver 67 converts a standard logic level signal of TTL (Transistor-Transistor Logic), CMOS (Complementary Metal-Oxide Semiconductor), and the like into a positive/negative voltage pulse signal of several-ten V necessary for causing a dielectrophoretic force. The driver 67 is a high-speed high-pressure switching device constituted of, for example, a complementary-type MOSFET (Field Effect Transistor).

The AC coupling capacitor 68 removes a DC component from the output voltage signal of the operation signal generation portion 60 so that a DC voltage is not applied to the operation electrode portion 40.

(Electric Field Formed by Operation Electrode Portion)

Figure 7:
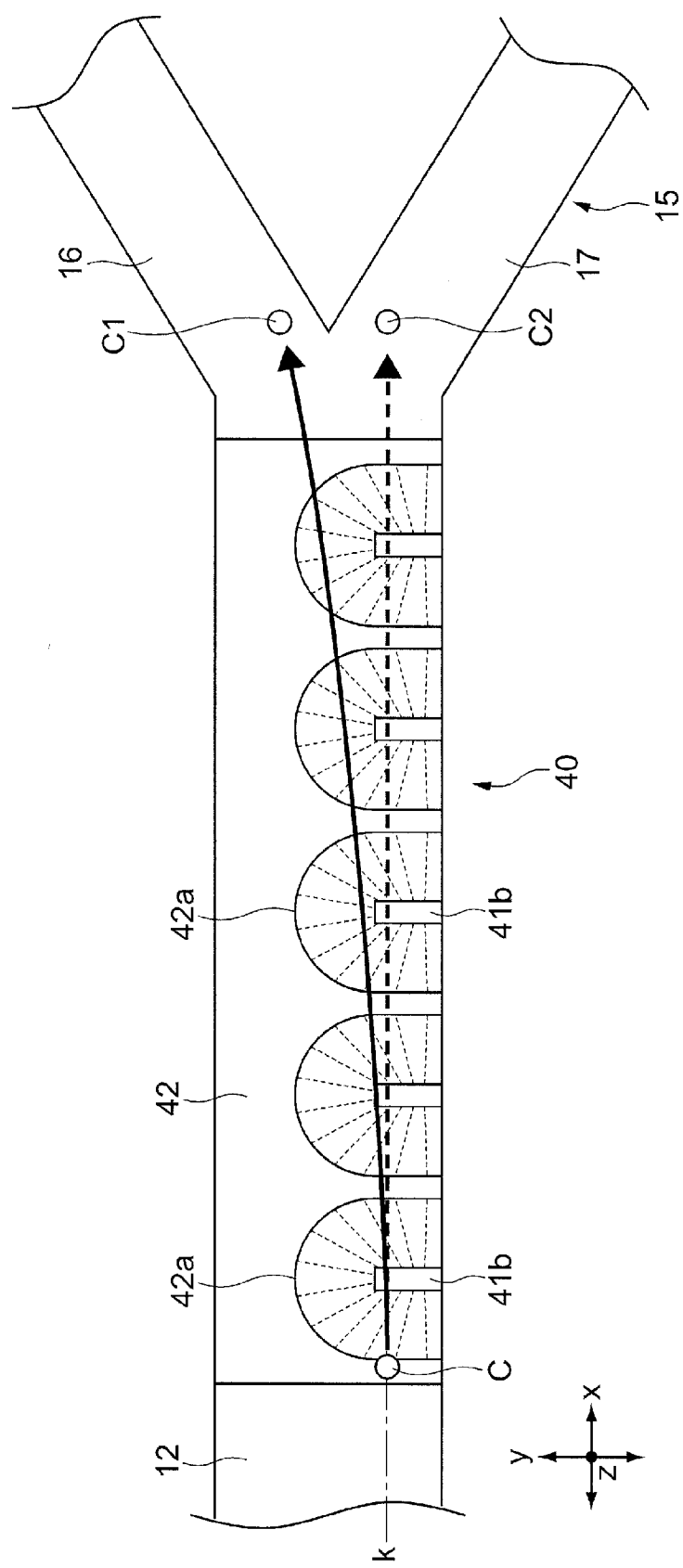
FIG. 7 is a diagram showing a state where particles are sorted by the flow channel device.

FIG. 7 is a diagram showing a state where particles are sorted. In FIG. 7, an electric field generated by the operation electrode portion 40 using an AC voltage output by the operation signal generation portion 60 is indicated by a broken line. While an electric flux density becomes high due to electric force lines concentrating on the electrode fingers 41b of the operation electrode 41, the electric flux density becomes smaller from the operation electrode 41 toward the edge portions 42a of the operation electrode 42. The dielectrophoretic force is dominated by an electric field intensity gradient, that is, a density change of the electric force line (or electric flux density), and the particles receive a force directed toward an area with a small electric flux density from an area with a high electric flux density. This point differs from the electrophoretic force that is generated in the direction along the electric force line. In other words, the dielectrophoretic force is not necessary caused in the direction along the electric force line.

Here, as shown in FIG. 3, the narrowed channel 13 is located at a position deviated in the width direction of the second flow channel 12 on a line K. On an extension of the line K on the downstream side, an area in which an electric field formed by the operation electrode portion 40 acts is provided.

As shown in FIG. 7, by the electric field intensity gradient generated by the operation electrode portion 40 as described above, a dielectrophoretic force in the y direction is applied to the particles C that have flown into the area where the operation electrode portion 40 is provided. Moreover, a force of the flow of the fluid is applied to the particles C also in the x direction. Accordingly, the particles C flowing along the line K from the narrowed channel 13 can change its' trajectory to flow toward the branch channel 16.

The dielectrophoretic force of this embodiment may take various values depending on parameters of a target particle size, structure, fluid medium, flow channel structure, and the like.

According to the operation electrode portion 40 having such a structure, since the electrode fingers 41b and the edge portions 42a are provided consecutively in the direction in which the fluid flows, the electric flux densities in the same state are aligned in the flowing direction for each of the electrode fingers 41b. Therefore, the operation electrode portion 40 can impart a minute displacement in the y direction stepwise to the particles little at a time.

(Operation of Sorting Apparatus)

A fluid including the particles C flows into the first flow channel 11 via the first inlet 11a and flows through the first flow channel 11. On the other hand, a fluid not including particles flows through the second flow channel 12. The particles C that flow through the first flow channel 11 join the flow of the second flow channel 12 via the narrowed channel 13.

A predetermined AC voltage is applied to the measurement electrodes 21 and 22 while the sorting apparatus 100 is being operated, and the measurement data generation portion 72 calculates a complex permittivity as described above and outputs it as measurement data when the particles pass the narrowed channel 13. As described above, the judgment portion 73 judges whether the particles are to be guided to the branch channel 16 based on the acquired measurement data.

When judged that the particles are to be guided to the branch channel 16, the operation signal generation portion 60 generates a predetermined operation voltage and applies the operation voltage to the operation electrode portion 40 right before the particles flowing through the second flow channel 12 reach the operation electrode portion 40. As a result, as shown in FIG. 7, an electric field is formed by the operation electrode portion 40, and the particles C changes its' trajectory by a dielectrophoretic force corresponding to the electric field to flow into the branch channel 16 as indicated by the symbol C1.

It should be noted that since the speed of the fluid including the particles and the distance between the narrowed channel 13 and the operation electrode portion 40 are determined in advance, the controller 70 can detect a timing right before the particles reach the operation electrode portion 40.

When judged that the particles are to be guided to the branch channel 17, the operation signal generation portion 60 does not generate an operation voltage. Therefore, a dielectrophoretic force caused by an electric field is not generated, and the particles move along the line K as they are and flow into the branch channel 17 as indicated by the symbol C2.

By the operation of the sorting apparatus 100 as described above, it is possible to distinguish normal cells and dead cells from each other or normal cells and cancer cells from each other, for example.

(Generation of Dielectrophoretic Force Using Operation Voltage Output by PDM Method)

Figure 8:
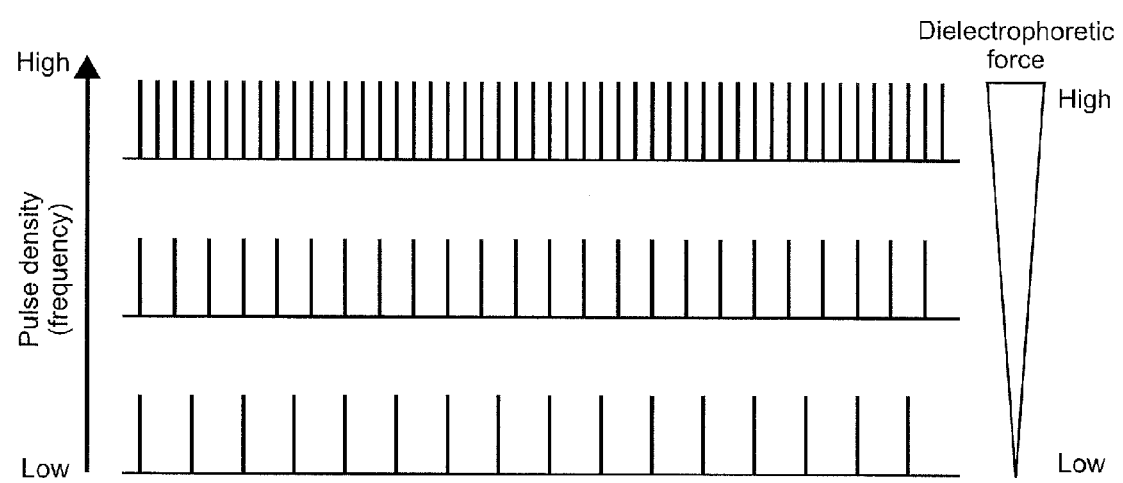
FIG. 8 is a diagram schematically showing a relationship between a pulse waveform output from the operation signal generation portion adopting a PDM method and a dielectrophoretic force.

FIG. 8 is a diagram schematically showing a relationship between a pulse waveform output from the operation signal generation portion 60 adopting the PDM method and a dielectrophoretic force. In the PDM, a pulse amplitude and a pulse width are constant, and the output voltage is controlled by adjusting a pulse count per unit time. The operation voltage becomes larger as the pulse density increases, and the dielectrophoretic force to be applied to the particles also becomes larger therewith.

Figure 9A:
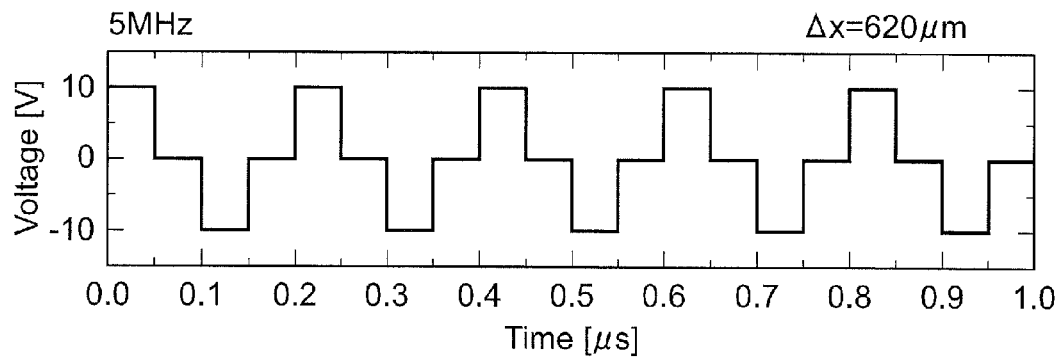
FIGS. 9A to 9C are diagrams showing the pulse waveforms output from the operation signal generation portion for each set frequency.
Figure 9B:
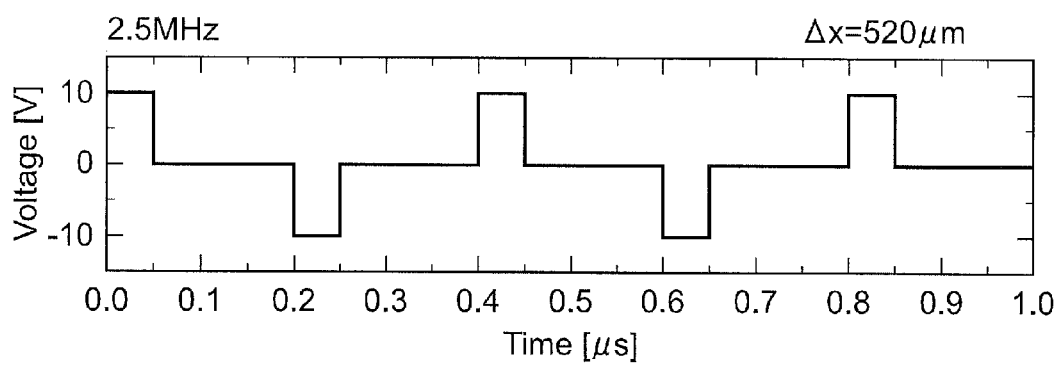
Figure 9C:
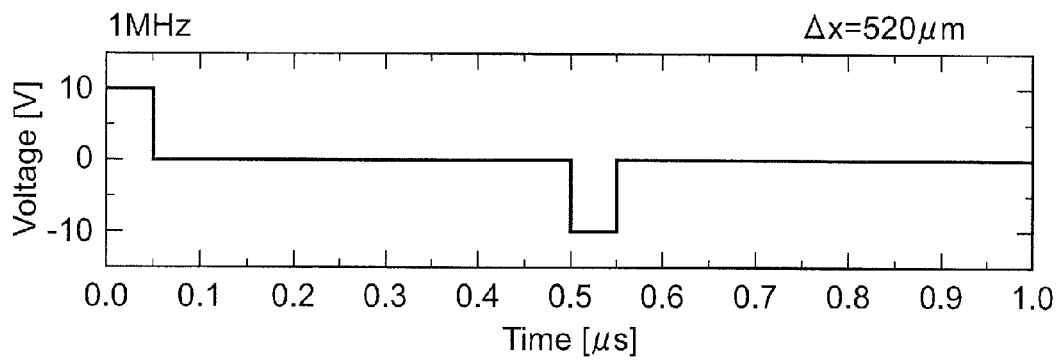

The inventors of the present disclosure applied an operation voltage under PDM control to the operation electrode portion 40 and actually measured a displacement amount of the particles (cells). FIGS. 9A to 9C are diagrams showing the pulse waveforms output from the operation signal generation portion 60 for each set frequency in the experiment.

The frequency is 5 MHz in FIG. 9A, 2.5 MHz in FIG. 9B, and 1 MHz in FIG. 9C, that is, 3 patterns of pulse densities were set. In the 3 patterns of frequencies, the pulse width was set to be constant at 50 ns, and the overall positive/negative amplitude (Vpp) was set to 20 V. For the frequencies shown in FIGS. 9A to 9C, the displacement amounts Δx of the particles in the x direction (direction in which fluid flows) were 620 μm, 520 μm, and 520 μm, respectively.

Figure 10A:
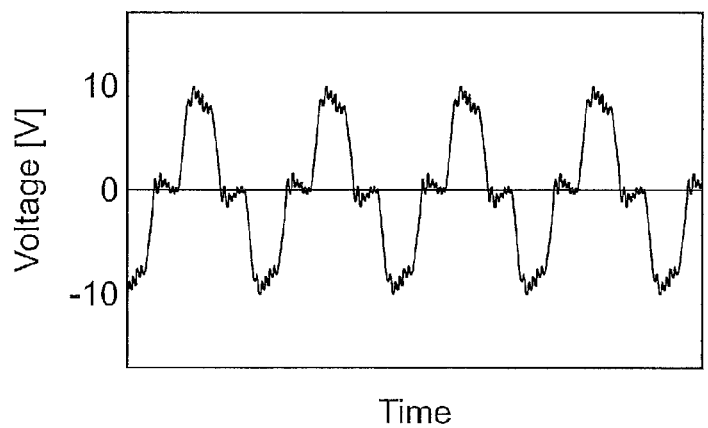
FIGS. 10A to 10C are diagrams showing the pulse waveforms of an operation voltage signal actually obtained by an oscilloscope, the pulse waveforms respectively corresponding to FIGS. 9A to 9C.
Figure 10B:
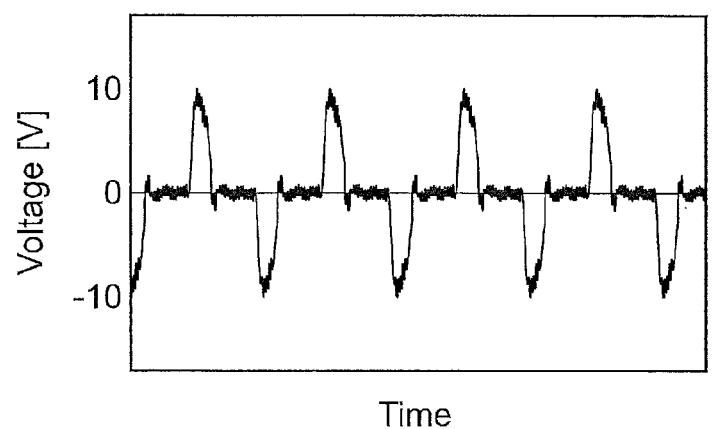
Figure 10C:
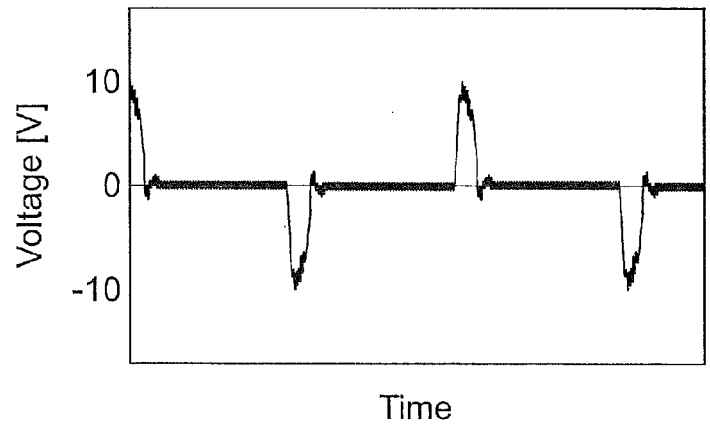

FIGS. 10A to 10C are diagrams showing the pulse waveforms of an operation voltage signal actually obtained by an oscilloscope, the pulse waveforms respectively corresponding to FIGS. 9A to 9C.

Figure 11:
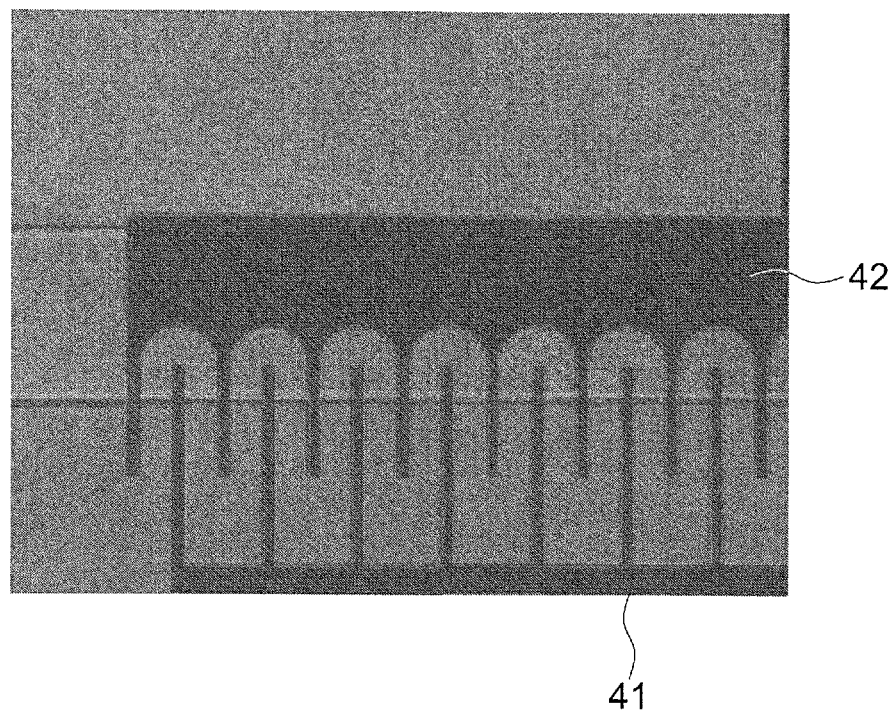
FIG. 11 is a photograph showing a flow channel and operation electrode portion used in an experiment.

FIG. 11 is a photograph showing the flow channel and operation electrode portion used in the experiment (seen in z direction).

z-direction height of flow channel: 17.1 μm
y-direction width of flow channel: 200 μm
Particle diameter: 12 μm
Flow rate: 1.2 μL/min
Mean flow speed: 5848.0 μm/s Moreover, referring to FIG. 4, the sizes a, b, and c of the operation electrode portion 40 used in the experiment were as follows.

Width a of electrode finger 41b of operation electrode 41: 10 μm

Figure 12:
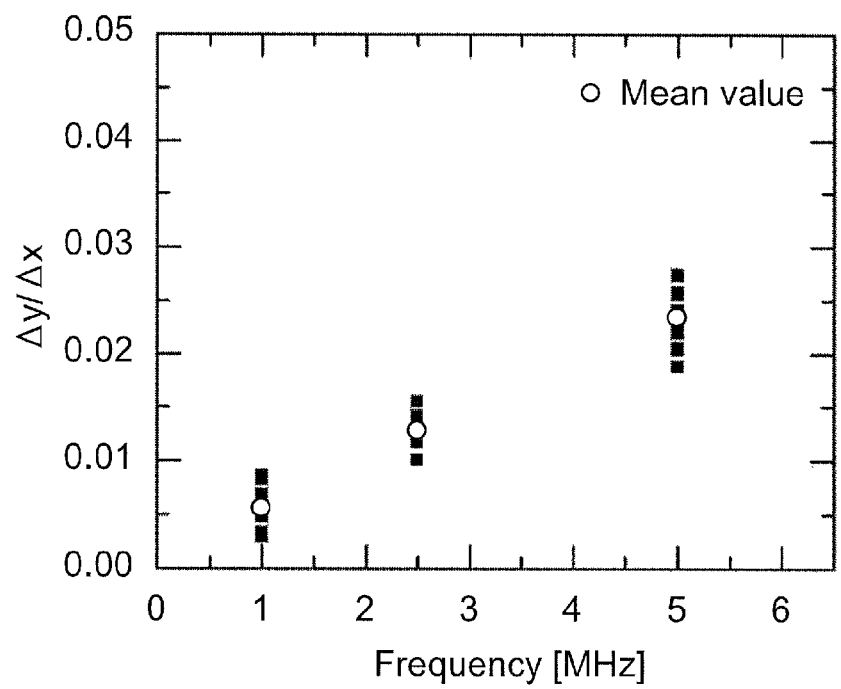
FIG. 12 is a graph showing a displacement amount ($\Delta y/\Delta x$) of synthetic particles in x and y directions for each of the set frequencies.

Distance b from tip end portion of electrode finger 41b of operation electrode 41 to edge portion 42a: 40 μm Width c of edge portion 42a of operation electrode 42: 10 μm FIG. 12 is a graph showing a displacement amount (Δy/Δx) of synthetic particles in the x and y directions for each of the set frequencies. The x direction is the direction in which the fluid flows, and the y direction is the direction in which the dielectrophoretic force acts. The flow speed of the fluid is about 7 mm/s. As the frequency becomes higher, that is, as the pulse density increases, the displacement amount of the particles in the y direction increases. It was found from the experiment that the dielectrophoretic force can be controlled by the PDM control, and as a result, the displacement amount of the particles can be controlled.

Figure 13:
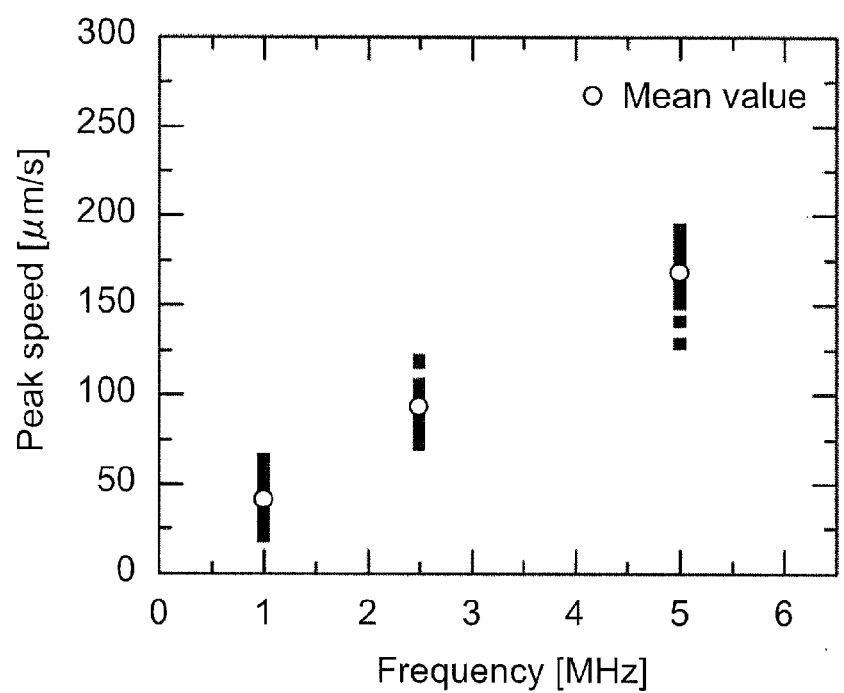
FIG. 13 is a graph showing a speed peak value of the particles in the y direction for each of the set frequencies.

FIG. 13 is a graph showing a speed peak value of the particles in the y direction for each of the set frequencies. As described above, the x direction is the direction in which the fluid flows, and the y direction is the direction in which the dielectrophoretic force acts. The flow speed of the fluid is about 7 mm/s. As the frequency becomes higher, that is, as the pulse density increases, the displacement amount of the particles in the y direction increases. It was found from the experiment that the dielectrophoretic force can be controlled by the voltage output by the PDM method, and as a result, the speed of the particles in the y direction can be controlled.

FIG. 14 is a table showing mean values of the particle displacement amounts (Δy/Δx) and the particle speeds in the y direction for each of the set frequencies regarding the experiments shown in FIGS. 12 and 13.

In the sorting apparatus, for maintaining existences of cells or living substances, it is necessary to measure electrical characteristics of the particles in an electrolyte solution such as a normal saline solution. However, in the electrophoresis caused by a DC electric field or the dielectrophoresis of a low frequency (smaller than 0.1 MHz) described above, an electrochemical reaction (electrolysis) occurs, and a damage of the electrodes and gas generation become a problem. Therefore, for obtaining an electrophoresis effect in the cells or living substances in the fluid by an electromagnetic force, a sine wave AC having a frequency of 0.1 MHz or more and an amplitude of several-ten V becomes necessary. However, for obtaining a sine wave AC having a frequency of 0.1 MHz or more and an amplitude of several-ten V, a high-frequency power circuit is required, and the structure becomes complex and expensive.

In contrast, according to this embodiment, since a voltage signal is generated by a pulse modulation using a square pulse, the operation signal generation portion 60 can be structured by an inexpensive circuit under digital control. Therefore, the control of the output voltage to the operation electrode portion 40 can be performed with ease using an inexpensive circuit.

Specifically, the present disclosure bears the following effects (1) to (3).

(1) In the case of sine wave drive, an analog amplifier is necessary, but in the pulse method, an ON/OFF operation of a switching device such as a MOSFET is only necessary.

(2) Since the ON/OFF operation of the pulse can be flexibly controlled by the digital control circuit, control of the dielectrophoretic force also becomes flexible.

(3) Since the signal modulation is fully digitized, a simple and compact circuit structure can be used by generating a control signal by, for example, FPGA (Field Programmable Gate Array) or CPLD (Complex Programmable Logic Device).

Further, the sorting apparatus of this embodiment can generate a desired AC voltage within a desired frequency range without using a complex and expensive apparatus such as a programmable function generator and a programmable synthesizer.

(Difference Between General Pulse Modulation Circuit and Pulse Modulation Circuit of Present Disclosure)

Generally, a pulse modulation circuit may be used for drive of an AC motor or for a switching regulator as a power supply. These apparatuses supply energy to an object by a voltage amplitude. Regarding this point, the sorting apparatus of the present disclosure is also an apparatus that supplies energy called dielectrophoretic force to the particles and is thus the same as the AC motor or power supply.

However, the drive frequency of the pulse modulation circuit used for driving an AC motor is about several kHz to several-hundred kHz. Moreover, the drive frequency of the pulse modulation circuit used for a switching regulator is about several-ten kHz even in an apparatus that is operated by relative-small power. In the case of an apparatus that requires large power, the frequency becomes lower.

As described above, in the motor and switching regulator, the drive frequency of several-hundred kHz is a maximum value, and it is impossible to generate a square pulse having a predetermined frequency range of 0.1 MHz or more and 100 MHz or less as in the present disclosure. In the communication field, there is of course a case where a pulse modulation is performed using a frequency of an MH order or a frequency higher than the MHz order. However, the modulation in a communication apparatus is a modulation for communication and not for imparting energy to an object by a voltage amplitude.

In other words, the sorting apparatus of the present disclosure uses a special technique for generating a square pulse having a predetermined frequency range of 0.1 MHz or more and 100 MHz or less and causing a minute dielectrophoretic force. By causing a minute dielectrophoretic force within such a high frequency range, a minute displacement can be imparted to the particles in a micro flow channel such as the flow channel 10.

Second Embodiment

Figure 15:
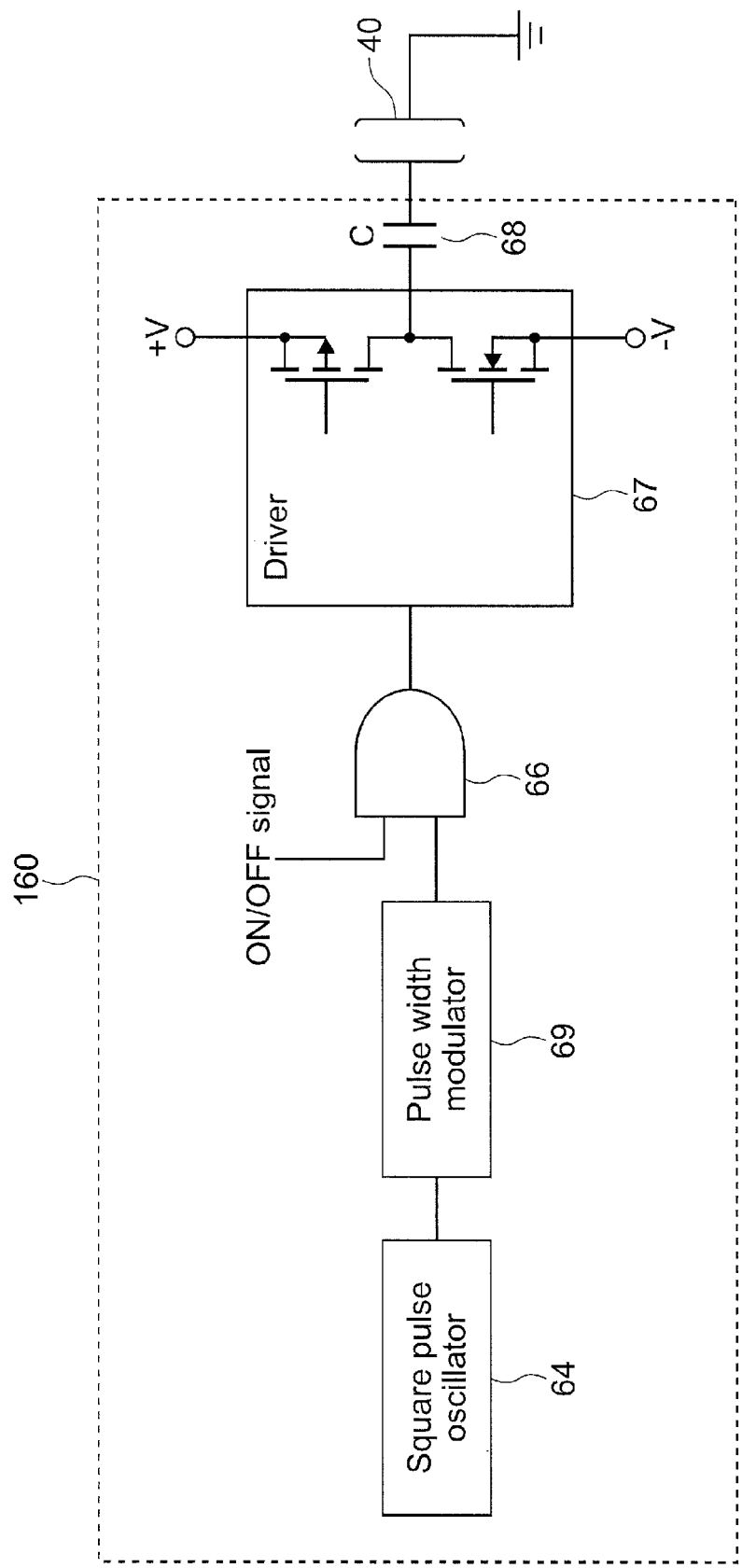
FIG. 15 is a block diagram showing a functional structure of an operation signal generation portion according to a second embodiment of the present disclosure.

FIG. 15 is a block diagram showing a functional structure of an operation signal generation portion according to a second embodiment of the present disclosure. In descriptions below, descriptions on members, functions, and the like that are the same as those of the sorting apparatus 100 according to the first embodiment will be simplified or omitted, and different points will mainly be described.

The operation signal generation portion 160 includes a pulse width modulator 69 for performing PWM (Pulse Width Modulation) in place of the counter 65 of the operation signal generation portion 60. The pulse width modulator 69 is capable of setting a desired duty ratio and outputting pulses while controlling a pulse cycle to be constant. The pulse cycle is of course not limited to the fixed cycle and may be variable.

It should be noted that in the case of this embodiment, the duty ratio of 0% plays a role of OFF for the switch 66. Therefore, the switch 66 is unnecessary.

Figure 16:
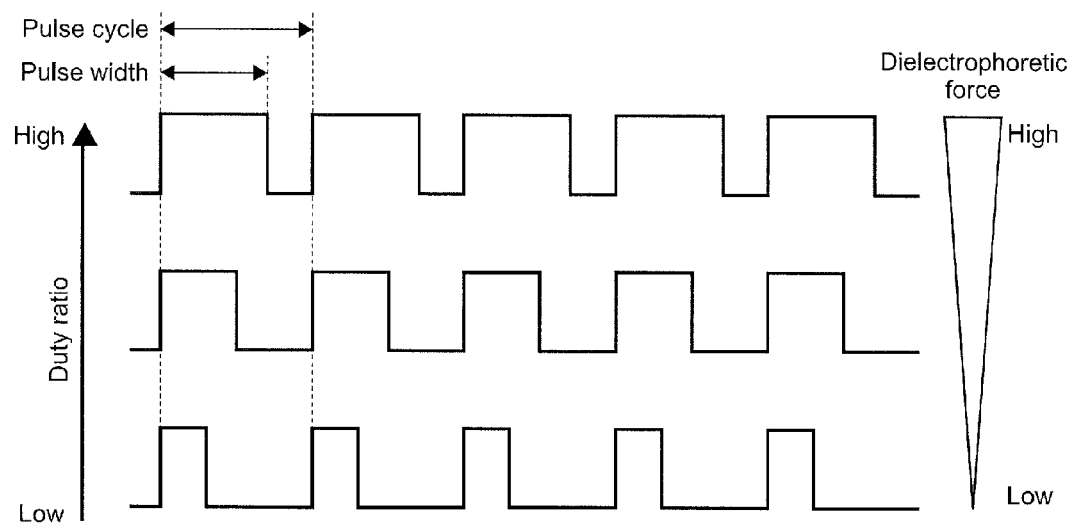
FIG. 16 is a diagram schematically showing a relationship between a pulse waveform output from the operation signal generation portion adopting a PWM method and a dielectrophoretic force.

FIG. 16 is a diagram schematically showing a relationship between a pulse waveform output from the operation signal generation portion 160 adopting the PWM method and a dielectrophoretic force. In the PWM, the dielectrophoretic force increases as the pulse width increases.

Other Embodiments

The present disclosure is not limited to the embodiments described above, and various other embodiments can also be realized.

The shape of the operation electrode portion 40 is not limited to the shape shown in FIGS. 3 and 4, and it is only necessary for the signal electrode to include a first surface area and the common electrode to include a second surface area different from the first surface area. It is favorable to secure a sufficient difference between the surface areas. Accordingly, an electric field intensity gradient is generated to cause a dielectrophoretic force.

The measurement electrode portion and the operation electrode portion of the embodiments above have been provided at positions that come into contact with the fluid in the flow channel 10, but they may be provided at positions that do not come into contact with the fluid, for example. For example, the operation electrodes 41 and 42 may be sandwiched between two resin films (not shown), and a flow channel may be provided on an upper surface of the upper-side one of films.

The controller 70 of the embodiments above has detected particle characteristics (electrical characteristics) by an electrical measurement using the measurement electrode portion 20 and the measurement device 71. However, the present disclosure is applicable to an apparatus that detects particle characteristics (type and size of particles) by irradiating laser light while causing particles to flow through a flow channel device and detecting scattering light or fluorescent light emitted from the particles onto which the laser light has been irradiated. Also in this case, the sorting apparatus only needs to generate a voltage signal by a pulse modulation using a square pulse based on the detected particle characteristics and output it to the operation electrode portion.

It should be noted that regarding an analysis apparatus for particles that uses laser light as described above, the applicant has filed Japanese Patent Application Laid-open No. 2009-063462, Japanese Patent Application Laid-open No. 2010-286341, Japanese Patent Application Laid-open No. 2011-095105, and many other patent applications.

Of the feature portions of the embodiments described above, at least two of the feature portions can be combined.

The present disclosure may also take the following structures.

(1) A sorting apparatus, including:

a flow channel device including a flow channel through which a fluid including particles flows and an operation electrode portion that causes a dielectrophoretic force to act on the particles in the flow channel; and a controller configured to detect characteristics of the particles flowing through the flow channel, generate a voltage signal by a pulse modulation using a square pulse based on the detected characteristics of the particles, and output the voltage signal to the operation electrode portion.

(2) The sorting apparatus according to (1),
in which the flow channel device includes a measurement electrode portion that measures electrical characteristics of the particles, and
in which the controller detects the characteristics of the particles based on a signal obtained by the measurement electrode portion.

(3) The sorting apparatus according to (2),
in which the controller calculates a complex permittivity based on the signal obtained by the measurement electrode portion and generates the voltage signal based on the complex permittivity.

(4) The sorting apparatus according to any one of (1) to (3),
in which the controller generates the voltage signal by PDM (Pulse Density Modulation).

(5) The sorting apparatus according to any one of (1) to (3),
in which the controller generates the voltage signal by PWM (Pulse Width Modulation).

(6) The sorting apparatus according to any one of (1) to (5),
in which the controller uses a square pulse having a predetermined frequency range of 0.1 MHz or more and 100 MHz or less.

(7) The sorting apparatus according to any one of (1) to (6),
in which the operation electrode portion includes
a plurality of electrode fingers to which the voltage signal is applied, the plurality of electrode fingers being aligned along a direction in which the fluid flows, and
an opposing electrode opposing the plurality of electrode fingers.

(8) The sorting apparatus according to (7),
in which the opposing electrode surrounds at least a part of a circumference of the plurality of electrode fingers such that a distance between tip ends of the plurality of electrode fingers and the opposing electrode becomes constant.

(9) A sorting method for sorting particles using a flow channel device including a flow channel through which a fluid including the particles flows and an operation electrode portion that causes a dielectrophoretic force to act on the particles in the flow channel, the method including:
detecting characteristics of the particles flowing through the flow channel; and
generating a voltage signal by a pulse modulation using a square pulse based on the detected characteristics of the particles, and outputting the voltage signal to the operation electrode portion.

It should be understood by those skilled in the art that various modifications, combinations, sub-combinations and alterations may occur depending on design requirements and other factors insofar as they are within the scope of the appended claims or the equivalents thereof.

What is claimed is:

1. A sorting apparatus, comprising:
a flow channel device that comprises a flow channel through which a fluid that includes particles configured to flow and an operation electrode portion configured to cause a dielectrophoretic force to act on the particles in the flow channel,
wherein the flow channel comprises a first flow channel and a second flow channel parallel to each other and are in communication with each other through a narrow channel;
a measurement electrode portion, wherein the measurement electrode portion further comprises the narrow channel sandwiched between a first electrode and a second electrode, wherein the first electrode and the second electrode are used for measurement of characteristics of the particles passes through the narrow channel; and
a controller configured to detect the characteristics of the particles that flows through the flow channel, generate a voltage signal by a pulse modulation by use of a square pulse based on the detected characteristics of the particles, and output the voltage signal to the operation electrode portion.

2. The sorting apparatus according to claim 1,
wherein the measurement electrode portion is configured to measure electrical characteristics of the particles, and
wherein the controller is configured to detect the characteristics of the particles based on a signal obtained by the measurement electrode portion.

3. The sorting apparatus according to claim 2, wherein the controller is configured to calculate a complex permittivity based on the signal obtained by the measurement electrode portion and generate the voltage signal based on the complex permittivity.

4. The sorting apparatus according to claim 1, wherein the controller is configured to generate the voltage signal by PDM (Pulse Density Modulation).

5. The sorting apparatus according to claim 1, wherein the controller is configured to generate the voltage signal by PWM (Pulse Width Modulation).

6. The sorting apparatus according to claim 1, wherein the controller is configured to use the square pulse that has a predetermined frequency range of 0.1 MHz or more and 100 MHz or less.

7. The sorting apparatus according to claim 1,
wherein the voltage signal is applied to a plurality of electrode fingers, and
wherein the plurality of electrode fingers are aligned along a direction in which the fluid flows.

8. A sorting method, comprising:
in a flow channel device:
measuring characteristics of particles passing through a narrow channel using a measurement electrode portion, wherein the measurement electrode portion comprising a first electrode and a second electrode sandwiching the narrow channel;
detecting the characteristics of the particles flowing through a flow channel,
wherein the flow channel comprises a first flow channel and a second flow channel parallel to each other and are in communication with each other through the narrow channel; and
generating a voltage signal by a pulse modulation using a square pulse based on the detected characteristics of the particles, and outputting the voltage signal to the operation electrode portion.

9. The sorting apparatus according to claim 1, wherein the operation electrode portion comprises:
an opposing electrode that opposes a plurality of electrode fingers, wherein the opposing electrode surrounds at least a part of a circumference of each of the plurality of electrode fingers such that a distance between a tip end of each of the plurality of electrode fingers and the opposing electrode is constant.

10. The sorting method of claim 8, wherein the operation electrode portion comprises an opposing electrode opposing a plurality of electrode fingers, wherein the opposing electrode surrounds at least a part of a circumference of each of the plurality of electrode fingers such that a distance between a tip end of each of the plurality of electrode fingers and the opposing electrode is constant.

\* \* \* \* \*